[19] United States Patent
Baiocchi

[11] 4,096,177
[45] Jun. 20, 1978

[54] PROCESS FOR THE PREPARATION OF P-ISOBUTYL-HYDRATROPIC

[76] Inventor: Leandro Baiocchi, via B. Platina 22, Rome, Italy

[21] Appl. No.: 746,114

[22] Filed: Nov. 30, 1976

Related U.S. Application Data

[63] Continuation of Ser. No. 519,769, Oct. 31, 1974, abandoned.

[30] Foreign Application Priority Data

Apr. 11, 1974 Italy .............................. 50315 A/74

[51] Int. Cl.$^2$ .............................................. C07C 63/04
[52] U.S. Cl. .................................. 260/515 R; 560/176

[58] Field of Search ..................................... 260/515 R

[56] References Cited

U.S. PATENT DOCUMENTS 3,852,286  12/1974  Hall et al. ........................ 260/515 A
4,008,270  2/1977   White ............................... 260/515 R Primary Examiner—Jane S. Myers

[57] ABSTRACT

A process for the synthesis of Ibuprofen, p - isobutyl hydrotropic acid is described based upon the aromatization reaction which takes place when a dialkyl α-acetyl-α-[(5-methyl-3-oxo)-hexyl]-α'-methyl-succinate (II) is heated at temperatures of about 200° with a strong acid, or a salt of a strong acid with an organic base.

1 Claim, No Drawings

PROCESS FOR THE PREPARATION OF P-ISOBUTYL-HYDRATROPIC

This is a continuation of application Ser. No. 519,769, filed Oct. 31, 1974, now abandoned.

This invention deals with a new process of synthesis of p-isobutyl-hydratropic acid, or 2-(4-isobutyl-phenyl)-propionic acid (I)

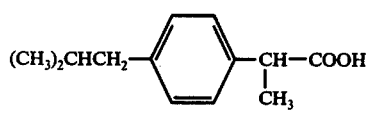

With the generic name "Ibuprofen", compound (I) is much used in therapy as an antiinflammatory, analgesic and antirheumatic agent As far as we know, there are four methods of synthesis, patented or described in the literature. The first of them (Brit. Pat. 971,700, 1964) consists in the transformation of p-isobutyl-acetophenone, by means of a Willgeredt reaction, into 1-(4-isobutyl-phenyl)-acetic acid. The acid is then esterified, reacted with ethyl carbonate and transformed into diethyl-2-(4-isobutyl-phenyl)-malonate. A methylation is then carried out with methyl iodide, followed by a hydrolysis and successive decarboxylation. The French Pat. No. 1,545,270, 1968, describes the transformation of p.isobutyl-acetophenone into 3-(4-isobutyl-phenyl)-2,3-epoxybutyric ester by means of ethyl chloroacetate. The product is then hydrolized and transformed into 2-(4-isobutyl-phenyl)-propanal by thermic decomposition. This aldehyde is then oxidized to the corresponding acid with $AgNO_3$, anhydrous potassium butylate or permanganate. The third method, claimed in the French Pat. No. 1,549,728, 1968, transforms p.isobutyl-acetophenone into the corresponding hydantoin with ammonium carbonate and potassium cyanide in aqueous ethanol solution. They hydantoin is hydrolyzed to aminoacid and the latter is then deaminated to give compound (I).

From a simple examination of the three above methods it appears evident that the second and third of them require the use of expensive or dangerous reactants, such as silver nitrate or potassium cyanide, while also the first method, which would be more suitable for an industrial preparation, seems to be rather complicated.

In all three methods, however, the starting product, which is already aromatic, is the same: p.isobutyl-acetophenone. The fourth method is described in the Brit. Pat. No. 1,265,800. It starts with the synthesis of methyl or ethyl 2-(4-isobutyl-2-oxocyclohex-3-enyl)-propionate. The processes for the preparation of these substances, mentioned in said patent, obtain them only as by-products and the yields are not reported. These substances, or the corresponding acid, are then aromatized to p.isobutyl-hydratropic acid by heating them with pyridine hydrochloride. Since neither the yields of this second operation are reported in the patent, we repeated the experiments mentioned in examples 2, 4, 8 and 12 in our laboratories, obtaining, however, very poor quantities of the products therein described (yields inferior to 5%). The conclusion of our experiments is that the method reported in the Brit. Pat. No. 1,265,800 for the synthesis of p.isobutyl-hydratropic acid has no possibility of industrial application. The method which is the object of the present invention does not require the use of expensive or dangerous reactants, nor the difficult preparation of 2-(4-isobutyl-2-osocyclohex-3-enyl) propionic acid. It is in fact based on an original aromatization reaction, of which we have no previous information in the literature, which takes place when a dialkyl α-acetyl-α-[(5-methyl-3-oxo)-hexyl]-α'-methyl-succinate (II) is heated at temperatures of about 200° with a strong acid, for example hydrochloric acid, hydrobromic acid, sulfuric acid, chlorosulfonic acid, p.toluenesulfonic acid, in aqueous solution; or, when dry, with a salt of a strong acid with an organic base as, for example, triethylamine, pyridine or other pyridine bases, quinoline, isoquinoline or their derivatives, as halohydrates, arylsulfonates, trifluoroacetates, methanesulfonates or mixtures with arylsulfochlorides.

The molar rates between the reactant and (II) range between 3 and 10, according to the different cases, and the heating times do not exceed 3 hours.

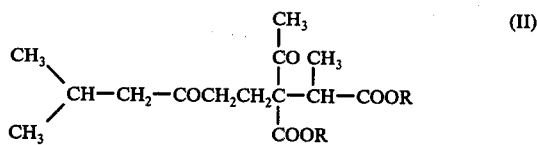

Derivatives corresponding to formula (II) in which R represents (H) or a lower alkyl group (1 to 5 carbon atoms) and in which the two alkyls can also be different one from the other, are not described in the literature. They can, however, be easily prepared in different ways. It is possible, for example, to start from ethyl α-acetyl-α'-methyl-succinate, known since 1881 (Ann. 206, 320) and react this product with isobutyl-vinyl-ketone (J. Org. Chem. 32, 1234, 1967). Instead of isobutyl-vinyl-ketone, the corresponding Mannich base, or a quaternary derivative of that base, can be reacted. Methyl, propyl, butyl or amyl esters can also be used instead of ethyl esters: isobutyl-vinyl-ketone can also be condensed first with acetoacetic ester, introducing then the residue of the halopropionic ester. In a very convenient method for industrial preparation, of which we are reporting some non restrictive examples, even the isolation of compound (II) is avoided. Such product can thus be obtained by treating acetoacetic ester with an alkyl α-halopropionate and isobutyl-vinyl-ketone, treating then the reaction mixture with aqueous HCl, or with another one among the acidic reactants previously mentioned.

It must be noted that compounds (II), also when the two alkyls are equal, are always mixtures of diastereomers. In one case — that is when R represents an ethyl group — the two couples of diastercomers were separated by column chromatography and each of the two couples was submitted to acidic treatment, according to the present invention. No difference in the yield of p.isobutyl-hydratropic acid was noticed either starting from one or the other of the two couples.

EXAMPLE 1 ethyl α-acetyl-α[(5-methyl-3-oxo)-hexyl]-α'-methyl succinate

Ethyl α-acetyl-α'-methyl-succinate (20 g – 0.087 moles) is added to a solution of sodium (100 mg) in anhydrous ethanol (20 ml) then, cooling the solution with ice and water, and drop by drop, vinyl-isobutylketone of recent preparation (10 g – 0.086 moles) is added.

The solution is kept under stirring for 3–4 hours at room temperature, then it is poured into water, extracted with ether and dried on sodium sulfate. It is distilled collecting, after some heads, a colourless oil (14 g) b.p. 170°–177° at 0.7 mm Hg.

Analysis: calc.: C, 63.13; H, 8.83. for $C_{18}H_{30}O_6$ found: C, 63.45; H, 8.53.

From the examination on Thin Layer Chromatography (silica - eluant: hexane-ether 1:1) the distilled product appears to be formed by the two couples of diastereomers (A and B): four additional, different products are also noticed, which were present in a negligible quantity and were not further examined.

EXAMPLE 2

Chromatographic separation of the two couples of diastercomers A and B

A chromatographic column 90 cm high and having a diameter of 5 cm with 900 g of Merck silica gel 70–230 mesh, was prepared. The retention volume was of 1400 ml of a solvent formed by a mixture of cyclohexane-ether 6:4. The 14 g. of the distilled product mentioned in example 1 were dissolved in ether (15 ml) and added to the column, prepared as above. Fractions of 25 ml each were collected.

After 69 fractions containing the retention volume and the solvent, the following products were obtained:
fraction 70 to 74 1 g of a colourless oil: impurity.
fraction 75 to 97 4.5 g of a colourless oil: couple A.
fraction 98 to 104 1 g of a colourless oil: mixture A + B.
fraction 105 to 122 4.5 g of a colourless oil: couple B.
fraction 123 to 132 1 g of oil: couple B + tail impurity.
fraction 133 to 137 0.4 g of a colourless solid: tail impurity.
fraction 138 to 148 0.6 g of a colourless solid: tail impurity.

The checking of the single fractions was effected on T.L.C. silica Merck F 254.

| Eluant | Rf A | Rf B |
|---|---|---|
| hexano-ether 1–1 | 0.35 | 0.25 (solvent run equal to 10 cm) |
| hexano-ether 6–4 | 0.45 | 0.35 (double elution- solvent run equal to 15 cm) |
| Detectors: | a) iodine vapours b) 57 solution of sulfuric acid (5′ at 110°) c) 10% ethanol solution of phosphomolibdic acid (5′ at 110°) | |

The elementar analysis and the NMR spectrum of couples A and B were in accordance with their structure.

EXAMPLE 3

Ethyl α-acetyl-α-[(5-methyl-3-oxo)-hexyl]-α′-methyl succinate (10 g) obtained as described in example 1 (b.p. 170°–177° at 0.7 mm) and 36% HCl (50 ml) were heated at 230° for 1 hour and a half in a sealed tube. After cooling, the tube was opened, the solution was diluted in water and extracted with ether. The ethereal extract was shaken with a 10% NaOH solution. The alkaline, clear solution was then brought to pH 6.5–7 with HCl, extracted with ether and then made strongly acidic. p.isobutyl-hydratropic acid was then separated, filtered, washed and dried. g 4.8 of the product were obtained m.p. 71°–3°. Similarly, p.isobutyl-hydratropic acid was also obtained by heating (II) in a sealed tube with 47 and 35% hydrobromic acid, with 35% sulfuric acid, with 30% chlorosulfonic acid, with 35% p.toluenesulfonic acid, at temperatures ranging between 200° and 230° for periods varying from 45 minutes to 1 hour and a half.

EXAMPLE 4

Ethyl α-acetyl-α-[(5-methyl-3-oxo)-hexyl]-α′-methyl succinate was added to pyridine hydrochloride (30 g): the solution was heated in a bath keeping the temperature at 230° and, at this temperature, the mixture was kept under stirring for 1 hour and a half. The solution was cooled, the brown mass was dissolved in water (100 ml) and the brown oil which separated was extracted with ether. The ethereal extract was shaken with a 10% NaOH solution: the alkaline, clear solution was acidified with HCl 1:1; p.isobutyl-hydratropic acid was separated as small particles of a greyish solid which was filtered, washed with water and dried. 5.3 g of the product were obtained. m.p. 691°–71°. The m.p. rose to 74°–75° when the product was crystallized from petroleum ether.

In the course of similar experiments, ethyl α-acetyl-α-[(5-methyl-3-oxo)-hexyl]-α′-methyl succinate, was treated with quinoline hydrochloride, with α-picoline hydrochloride and hydrobromide, with triethylamine hydrochloride, with isoquinoline hydrochloride, with pyridine benzenesulfonate, or p.toluenesulfonate, or naphtalenesulfonate or methanesulfonate or trifluoroacetate, at temperatures ranging between 200° and 240°, for periods varying from 1 to 2 hours. In every case, p.isobutyl-hydratropic acid was obtained with good yields.

EXAMPLE 5

Ethyl α-acetyl-α′-methyl-succinate (10 g) was added, all at once, to sodium (50 mg) dissolved in anhydrous ethanol (10 ml). Then, after cooling with ice and under stirring, recently prepared vinyl-isobutyl-ketone (10 g) was added, drop by drop. The mixture was kept under stirring for 4 hours at room temperature, then it was poured into a 500 ml flask containing pyridine hydrochloride (60 g) and the mixture was heated at 230° for 1 and a half under stirring. The brown mass was cooled, dissolved in water (150 ml) and extracted with ether; the ethereal extracts were shaken with 10% NaOH (100 ml) and the alkaline solution, diluted with water (500 ml) was acidified with HCl 1:1 (45 ml). p.isobutyl-hydratropic acid was separated as small particles of a brownish solid, which was filtered, washed with water and dried. Yield: 7 g m.p. 69°–71°.

EXAMPLE 6

Methyl acetoacetate (22.5 g) was added to a solution of sodium (4:5 g) in anhydrous ethanol (100 ml). The solution was heated under reflux for 5 mins., cooled and, after addition of ethyl α-bromopropionate (35 g) refluxed, under stirring, for 5 hours.

The solution was then cooled, filtered from sodium bromide and, after removing most of the alcohol under reduced pressure, poured into a small quantity of water. The oil which separated was extracted with ether and dried on sodium sulfate. After evaporation of the solvent an oily residue (35 g) was obtained which was added to a solution of sodium (175 mg) in anhydrous ethanol (35 ml). Vinyl-isobutyl-ketone (35 g) was added, drop by drop, to the cooled solution, letting it under stirring, at room temperature, for 3 hours, then one night at rest. The reaction product as such was poured into a 1000 ml flask containing α-picoline hydrochloride (210 g). The mixture was then kept for 1 hour and a half at 230° under stirring and cooled. The brown mass was dissolved in water (400–500 ml) and the oil which separated was extracted with ether. The ethereal extracts were concentrated to dryness, the brown residue was treated with 10% NaOH solution (200 ml) in which it was almost completely soluble. It was once more extracted with ether in alkaline medium, then the aqueous solution was acidified with HCl 1:1 (100 ml). p.isobutyl-hydratropic acid which separated was filtered, washed with water and dried. After crystallization from petrol ether 12 g of almost pure product were obtained.

EXAMPLE 7 t.butyl acetyl-acetate (10.5 g) was added to a solution of sodium (1.4 g) in anhydrous ethanol (40 ml). After heating under reflux for 5 minutes, the solution was cooled and ethyl αbromo-propionate (10 g) was added, heating then under reflux for 5 hours, under stirring. The solution was cooled, filtered from the sodium bromide which separated and most of the alcohol was removed under reduced pressure. It was then poured into water, the oil which separated was extracted with ether and dried on sodium sulfate. After evaporation of the solvent an oily residue was obtained (11.65 g) which was added to a solution of sodium (120 mg) in anhydrous ethanol (25 ml). Vinyl-isobutyl-ketone (10.5 g) was slowly added to the cooled solution, under stirring. The solution was kept at room temperature and under stirring for 3 hours and one night at rest; then it was poured into water, the pH was brought to about 6.5 with some drops of acetic acid and the solution was extracted with ether. The ethereal extracts, after drying on sodium sulfate, were concentrated under reduced pressure: the oily residue (12 g) was treated, in a sealed tube; with 47% hydrobromic acid (25 ml) for 1 hour and a half at 230°. The solution was cooled, diluted with water (150–200 ml) and extracted with ether. The ethereal extracts were shaken with a 10% NaOH solution (100 ml) and then with water. The aqueous alkaline solution was brought to pH 6, 5–7 with HCl 1:1 and extracted again with ether, then strongly acidified (red Congo indicator) again with HCl 1:1. p.isobutyl-hydratropic acid separated, which was filtered, washed with water and dried. Yield: 2.1 g.

EXAMPLE 8

Methyl α-acetyl-α'-methyl-succinate (J.Chem.-Soc.1933, 811) (5.8g) was added to a solution of sodium (35 mg) in anhydrous methanol (10 ml) and then, slowly and gradually cooling the solution, vinyl-isobutyl-ketone (6.5 g) was also added. The solution was kept under stirring, at room temperature, for 3 hours, then one night at rest. It was then poured into water, extracted with ether, and the extracts were dried on Na₂SO₄. After evaporation of the solvent a colourless oil was left, from which methyl α-acetyl-α-[(5-methyl-3-oxo)-hexyl]-α'-methyl-succinate was obtained with good yields. b.p. 145°–150° at 0.2 mm.

The analysis and the NMR spectrum were in accordance with the structure.

The distilled product which, similarly to what was described in example 1, was formed by the mixture of two couples of diastereomers, was treated with different acidic reactants, chosen among those mentioned in the general description of this patent, at temperatures of about 230°.

In all cases, p.isobutyl-hydratropic acid was obtained with good yields.

I claim:

1. A process for the preparation of p-isobutyl-hydratropic acid (I) which comprises the steps of heating at a temperature ranging from 200° to 240° C and for a period ranging from one-half to 3 hours, 1 mol of a compound of the formula

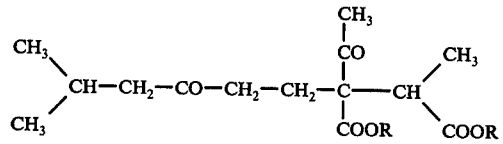

where each R represents a lower alkyl having from 1 to 5 carbon atoms, in the presence of 3 - 10 mols of a strong acid in aqueous solution or 3 to 10 mols of a salt of a strong acid with an organic base, where said organic base is selected from the group consisting of triethylamine, pyridine, picolines, quinoline and isoquinoline and then pouring said heated and thus reacted mixture into water and separating said p-isobutylhydratropic-containing product which segregates.

* * * * *